United States Patent [19]

Feldner et al.

[11] Patent Number: 5,015,751

[45] Date of Patent: * May 14, 1991

[54] PROCESS FOR THE PRODUCTION OF ORGANOCHLOROSILANES

[75] Inventors: Kurt Feldner, Leverkusen; Bruno Degen, Much; Gebhard Wagner, Odenthal; Manfred Schulze, Leichlingen, all of Fed. Rep. of Germany

[73] Assignee: Bayer Aktiengesellschaft, Leverkusen, Fed. Rep. of Germany

[ * ] Notice: The portion of the term of this patent subsequent to Jan. 23, 2007 has been disclaimed.

[21] Appl. No.: 439,726

[22] Filed: Nov. 20, 1989

[30] Foreign Application Priority Data

Dec. 8, 1988 [DE] Fed. Rep. of Germany ....... 3841417

[51] Int. Cl.$^5$ ................................................ C07F 7/16
[52] U.S. Cl. .................................................... 556/472
[58] Field of Search ........................................ 556/472

[56] References Cited

U.S. PATENT DOCUMENTS 3,133,109  5/1964  Dotson .
4,500,724  2/1985  Ward, III et al. .
4,895,969  1/1990  Feldner et al. ...................... 556/472

Primary Examiner—Paul F. Shaver
Attorney, Agent, or Firm—Sprung Horn Kramer & Woods

[57] ABSTRACT

In the production of organochlorosilanes by reaction of silicon with an alkyl- and/or arylchloride in the presence of a copper catalyst and, optionally, promoter elements, the improvement wherein the silicon has been atomized with an inert gas, has a particle size of less than about 1000 µm, by weight has an Al content of about 0.05 to 0.38%, a Ca content of about 0.02 to 0.2% and an Fe content of about 0.25 to 0.55%.

4 Claims, No Drawings

PROCESS FOR THE PRODUCTION OF ORGANOCHLOROSILANES

This invention relates to a new process for the production of organochlorosilanes by reaction of silicon atomized with inert gas with an alkyl- or arylchloride in the presence of a copper catalyst and promoter elements, More particularly, the invention relates to a process for the production of methylchlorosilanes.

The basic process for the production of methylchlorosilanes is the direct reaction of finely divided, ground silicon with methylchloride in the presence of metallic copper or, occasionally, silver as catalyst. The reaction is known to the expert as "Rochow's synthesis" and is described in U.S. Pat. No. 2,380,995.

A mixture of the following silanes (Me=CH$_3$) is mainly obtained in this process: Me$_2$SiCl$_2$, Me$_4$Si, Me$_3$SiCl, MeSiCl$_3$, SiCl$_4$, HSiCl$_3$3, MeHSiCl$_2$ and MeHSiCl. In addition to the monomeric methylchlorosilanes mentioned, higher-boiling compounds, such as for example methylchlorodisilanes, methylchlorotrisilanes, disiloxanes and silmethylenes, are also formed in relatively small quantities. In general, it is the monomeric compounds which are industrially used, dimethyldichlorosilane being of particular interest. Accordingly, it is desirable to obtain this preferred reaction product with the highest possible selectivity, a measure of selectivity being inter alia the ratio of MeSiCl$_3$ to Me$_2$SiCl$_2$ (the so-called tri:di ratio), the value of which should be as small as possible.

On an industrial scale, particular emphasis is placed on the production of methylchlorosilanes by reaction of methylchloride with silicon in a fluidized-bed reactor, methylchloride used in excess serving both as reactant and as fluidizing medium.

Since the first investigations about 40 years ago, there have been several publications describing processes for carrying out the reaction, for improving selectivity, for the production of suitable catalysts and catalyst/promoter systems. A first comprehensive review can be found, for example, in "Organohalosilanes: Precursors to Silicones", Voorhoeve, Elsevier Publishing Company, Amsterdam/New York/London, 1967.

The most recent works have concentrated mainly on the specific use of trace elements, so-called promoters, in the catalyst system, cf. for example DE-A-3 425 424, EP-A-138 678, EP-A-138 679, DE-A-3 501 085, EP-A-191 502, EP-A-194 214, EP-A-195 728, EP-A-223 447.

Comparatively few publications relate to the silicon and, when they do, are concerned with purity requirements and physical parameters, such as particle size distribution. For example, U.S. Pat. No. 3,133,109 states that particle sizes in the range from 20 to 200 $\mu$m are suitable for the optimal operation of a fluidized-bed reactor. In U.S. Pat. No. 4,500,724, silicon smaller than 700 $\mu$m is regarded as suitable, the mean particle size being said to be in the range from 20 to 300 $\mu$m and preferably in the range from 100 to 150 $\mu$m. The limits mentioned above count generally as state-of-the-art and experts know that the particular optimum is closely related to the particular reactor system used.

Now, the present invention relates to a process for the production of organochlorosilanes, characterized in that silicon which has been produced by atomizing with an inert gas or a suitable alloy of silicon which has been produced by atomizing with an inert gas is used, having thus been brought into a finely divided form in which it may directly be used for the production of organochlorosilanes.

The silicon atomized with an inert gas has a particle size of from 0.1 to 1000 $\mu$m, a specific BET surface of from 0.001 to 1 m$^2$/g and a chemical composition of (in % by weight) 0.05-1% Fe; 0.01-1% Al; 0.0001-1% Ca; 0-8% Cu; 0-1% Zn; 0-1% Sn; 0-0.5% B; 0-0.5% P; 0-0.5% Na; 0-0.5% Li; 0-0.5% K; 0-0.5% Mg; 0-0.5% Sr; 0-0.5% Ba; 0-0.5% Be, remainder silicon (or optionally other impurities in small amounts).

The silicon preferably contains 0.05-0.38% Al, 0.02-0.20% Ca and 0.25-0.55% Fe.

The atomizing of metals is a standard process for the production of metal powders and has long been applied, for example, to such metals as copper or its alloys. In most cases, metal powders produced in this way are further processed by standard powder-metallurgical techniques into shapes having particular properties; cf. Ullmanns Encyclopädie der technischen Chemie, 4th Edition, Vol. 19, page 566, Verlag Chemie, Weinheim, 1980.

In the atomizing technique, extremely short solidification and cooling times for the silicon are essential. It is also crucially important that the Si powder be atomized with an inert gas, for example nitrogen.

The fact that starting material thus produced shows considerably higher reaction velocity in the synthesis of organochlorosilanes is completely surprising and new.

For the synthesis of methylchlorosilane, the process according to the invention is carried out by reacting atomized silicon having a purity of greater than 98.5% and a particle size below 1000$\mu$ and preferably below 500 $\mu$m with methylchloride in the presence of a mechanically prepared mixture of copper catalyst and promoter elements. The process according to the invention is preferably carried out in a fluidized-bed reactor because by far the most favorable yields of desired product are obtained in this way and processing advantages, for example high heat transfer, can also be utilized.

In another preferred embodiment of the process, a silicon/copper alloy which has also been obtained by atomizing in an inert gas is reacted with methylchloride.

So-called promoter elements, providing they are used in metallic form, may of course also be added to the alloy to be atomized or may even be mechanically mixed with the atomized silicon/copper alloy.

In the latter case, a fluidized-bed reactor is again preferably used to carry out the reaction.

The silicon used in the process according to the invention has a purity of more than 98.5% Si and preferably more than 99% Si. It is particularly important that the Pb content of the silicon should not exceed 10 ppm. Since the reaction is preferably carried out in a fluidized-bed reactor in the process according to the invention, considerable significance is attributed to the physical properties of the silicon, such as for example its particle size distribution, in addition to its chemical properties. The silicon particles should generally be smaller than 1000$\mu$ and are preferably smaller than 500 $\mu$m, a particle size distribution of 30 to 300 $\mu$m for a mean particle size of 100 to 150 $\mu$m being particularly preferred.

The above-mentioned range for the preferred particle size distribution also applies to a suitable atomized silicon/copper alloy.

In the preferred embodiment of the process according to the invention for the production of methylchlorosilanes, 0.5 to 8 parts and preferably 1 to 3 parts catalyst/promoter mixture can be used to 100 parts silicon metal. However, this range may be varied within wide limits because the reaction is normally carried out continuously, rather than discontinuously, in a fluidized-bed reactor.

If an atomized alloy is used in accordance with the invention, its composition is selected as follows:
Si: 90 to 99% by weight
Cu: 0.5 to 8% by weight An atomized alloy and atomized silicon may of course both contain the typical impurities known to the expert, such as Fe, Al, Ca, Ti, etc., within the limits indicated above.

According to the invention, suitable promoter elements may be added to the melt to be atomized. Promoter elements are known to the expert, cf. the literature cited hereinabove where the elements zinc, tin and phosphorus are mentioned in particular.

The process according to the invention is carried out at a temperature in the range from 250° to 350° C. and preferably at a temperature in the range from 280° to 330° C.

It is advisable to carry out the process under a pressure above atmospheric pressure because the volume/time yield is increased in this way.

An excess pressure of up to 10 bar is advisable, an excess pressure of up to 5 bar being best.

These conditions provide for optimal selectivity in regard to the formation of dimethyldichlorosilane. In addition, it is possible in this way to obtain an optimally controllable reaction velocity.

The gaseous methylchloride is used in a large excess in the reaction because it is passed continuously through and fluidizes the catalyst mass of silicon metal particles and the catalyst/promoter mixture or through the atomized alloy.

The expert knows that it is not essential to use fluidized-bed reactors, particularly on a laboratory scale; instead it is common practice to use reactors in which the catalyst mass is vibrated during the reaction or is kept in motion by means of a helical stirrer to avoid local overheating and to guarantee safe conduct of the reaction.

As the numerous publications cited above show, attempts have hitherto been made to improve not only the selectivity, but also the yield of dimethyldichlorosilane via the catalyst/promoter system. However, it was found that the reaction velocity is also very sensitive to promoters and inhibitors. Thus, the invention according to DE-OS 3 425 424, page 10, is also concerned with the considerable increase in the rate of formation of dimethyldichlorosilane.

All the more surprising was the fact that the method by which the silicon is size-reduced (atomizing as opposed to grinding) should play such a key part. This effect is surprising and new.

The process according to the invention may of course also be used for the production of other organochlorosilanes. Any changes which may have to be made to the process parameters are familiar to the expert.

The invention is illustrated by the following Examples.

EXAMPLE 1

All the following experiments were carried out in a stirred-bed reactor of glass (internal diameter 30 mm) equipped with a helical stirrer. The same quantity of silicon or silicon/copper alloy having the same particle size distribution of 71 to 160 $\mu$m was used in every experiment. Methylchloride was passed through the catalyst mass from below through a glass frit under a pressure of 2 bar. The quantity of methyl chloride was kept constant and, in every case, amounted to approximately 1.5 l/h at 2 bar. After heating up and initiation of the reaction, a stationary experimental phase was established at 300° C. and the quantity of crude silane mixture formed per unit time was determined under the conditions thus established. The values shown are all mean values of four individual measurements under constant boundary conditions of 2 bar, 1.5 l/h methyl chloride and 300° C.

The catalyst mass consisted of 40 g silicon, 3.2 g copper catalyst and 0.05 g ZnO and was homogenized before use. The same catalyst was used in every case. Samples A and B are commercial silicon powders of different origin produced in the usual way by grinding. Sample C is a silicon powder produced by atomizing with nitrogen.

The following production rates in g/h crude silane mixture are obtained under comparable reaction conditions (2 bar, 1.5 l/h MeCl and 300° C.):
A: 5.7 g/h
B: 5.2 g/h
C 8.3 g/h (over a period of about 8 hours),
which corresponds to an increase in the production rate of approximately 45 and 56% through the use of atomized material.

EXAMPLE 2

An alloy produced by atomizing and having the following composition:
Fe: 0.34; Al: 0.40; Cu: 5.75; Zn: 0.14
(plus other non-analyzed impurities)
was reacted in the reactor described in Example 1 under the same conditions (2 bar, 1.5 l/h methyl chloride, 300° C.). In two experiments, the production rates of 8.13 g/h and 9.4 g/h were again distinctly above the otherwise typical production rates of 5 to 6 g/h.

EXAMPLE 3

Example 3 is intended to show that the rapid cooling is crucially important to the production rate.

Sample C of Example 1 is compared under the reaction conditions described above with a sample D of the same atomized material which has been subjected to a heat treatment before use in the direct synthesis. To this end, the sample—fused in vacuo in an ampoule—was heated for 2 hours at 1000° C. and then slowly cooled again over a period of another 6 to 8 hours.

Under the reaction conditions mentioned above, the following production rates are obtained for the reaction with methyl chloride (cf. Example 1):
Sample C (unheated): 8.3 g/h
Sample D (heated): 2.35 g/h
The composition of the catalyst mass was of course the same.

The Example shows a reduction in the production rate for crude silanes to around 28% compared with the original sample C, which is attributable solely to the heat treatment.

It will be appreciated that the instant specification and claims are set forth by way of illustration and not limitation, and that various modifications and changes may be made without departing from the spirit and scope of the present invention.

What is claimed is:

1. In the production of organochlorosilanes by reaction of silicon with an alkyl- and/or arylchloride in the presence of a copper catalyst and, optionally, promoter elements, the improvement wherein the silicon has been atomized with an inert gas has a particle size of less than about 1000 μm, by weight has an Al content of about 0.05 to 0.38%, a Ca content of about 0.02 to 0.2% and an Fe content of about 0.25 to 0.55%.

2. A process according to claim 1, wherein the atomized silicon is a Si/Cu alloy atomized with an inert gas.

3. A process according to claim 2, wherein the inert gas is nitrogen.

4. A process according to claim 1, wherein the silicon before atomization contains promoter elements.

* * * * *